United States Patent [19]

Turley

[11] 4,289,712

[45] Sep. 15, 1981

[54] TETRACHLORO-BUTYL SECONDARY PHOSPHITES

[75] Inventor: Richard J. Turley, Orange, Conn.

[73] Assignee: Olin Corporation, New Haven, Conn.

[21] Appl. No.: 164,737

[22] Filed: Jun. 30, 1980

Related U.S. Application Data

[62] Division of Ser. No. 80,744, Oct. 1, 1979, Pat. No. 4,247,489, which is a division of Ser. No. 937,033, Aug. 25, 1978, Pat. No. 4,207,272.

[51] Int. Cl.$^3$ ............................................. C07F 9/141
[52] U.S. Cl. .................................................. 260/967
[58] Field of Search ......................................... 260/973

[56] References Cited

U.S. PATENT DOCUMENTS 2,169,185  8/1939  Shoemaker et al. ................ 260/967

*Primary Examiner*—Anton H. Sutto
*Attorney, Agent, or Firm*—William D. Sabo

[57] ABSTRACT

Disclosed are novel tetrachloro-butyl secondary phosphites which are the reaction product of 4,4,4-trichloro-1,2-epoxybutane or 2,4,4,4-tetrachlorobutanol with a phosphorus trihalide. These compounds are useful as flame retardant additives in plastic resin compositions.

3 Claims, No Drawings

TETRACHLORO-BUTYL SECONDARY PHOSPHITES

This is a division of application Ser. No. 080,744, filed Oct. 1, 1979, now U.S. Pat. No. 4,247,489, which in turn is a division of application Ser. No. 937,033, filed Aug. 25, 1978, which is now U.S. Pat. No. 4,207,272 issued June 10, 1980.

Current and anticipated regulations restricting the flammability of plastic wares has required the manufacturers of plastic articles to implement effective ways to fire-retard these materials. Such efforts have produced a variety of fire retardant compounds which can be incorporated into the resin mixtures. Phosphorus and halogen additive compounds, in particular, have been found to impart favorable fire-retardancy properties.

Novel halogenated phosphite esters have now been developed, according to the present invention, which are useful as fire retardant additives for various plastic compositions. These chlorinated alkyl secondary phosphites offer a favorable balance of cost, fire retardance, and useful resin property modification.

The novel compounds of the present invention are secondary phosphite addition products of 4,4,4-trichloro-1,2-epoxybutane and 2,4,4,4-tetrachlorobutanol with a phosphorus trihalide.

The compound 2,4,4,4-tetrachlorobutanol (TCBA) is a well-known versatile compound with a wide range of utilities. It can be prepared by various conventional methods. For example, U.S. Pat. No. 3,399,217 describes a method for preparation of TCBA by the catalyzed reaction of carbon tetrachloride and allyl alcohol. TCBA reacts in a manner typical of aliphatic alcohols, and, in addition, may be readily dehydrohalogenated to yield the compound 4,4,4-trichloro-1,2-epoxybutane (TCBO). TCBO is a well-known reactive, high chlorine-containing epoxide useful in the preparation of epoxy resins, lubricants, polyurethane foams, and the like. An exemplary method for production of TCBO by dehydrohalogenation of TCBA is described in U.S. Pat. No. 3,923,844.

Secondary alkyl phosphites are commonly prepared by methods known in the art involving reaction of phosphorus trichloride with a primary alcohol (see Noller, *Chemistry of Organic Compounds*, Third Edition (1966), p. 318). Using stoichiometric proportions of reactants, i.e., about 3 moles of alcohol per each mole of phosphorus trichloride, the reaction results in the formation of a tertiary alkyl phosphite. In the absence of an amine base to scavenge the liberated hydrogen chloride gas formed during the reaction, the tertiary phosphite is cleaved by the action of the HCl to produce a secondary phosphite ester.

However, as pointed out in co-pending application Ser. No. 899,919, filed Apr. 26, 1978, it has surprisingly been discovered that in the reaction of TCBA and a phosphorus trihalide, the tertiary phosphite ester formed is not cleaved by the internally generated hydrogen halide under the normal reaction conditions, without application of external energy or increased pressure, and maintains its integrity even in the absence of an amine scavenger.

According to the present invention, the novel tetrachloro-butyl secondary phosphites can be prepared by a method involving reaction of a phosphorus trihalide with an alkylene oxide or alcohol comprising TCBA and/or TCBO and including a supplemental alcohol or alkylene oxide in substitution of a portion of the TCBA or TCBO reactant. This supplemental reactant forms an ester more susceptible to hydrogen halide attack than the TCBA or TCBO ester group and is selectively cleaved by the hydrogen halide to readily result in secondary phosphite formation.

More in detail, the reactions by which the present compounds can be made are represented by Equations I and II below. Equation I represents reaction of two moles of TCBA with one mole of phosphorus trichloride followed by addition of one mole of a supplemental alcohol (e.g., methanol) to produce a mixed tertiary phosphite ester which is transformed into the secondary phosphite by selective cleavage of the methyl ester by the internally generated HCl. The cooling effect of the HCl generated also serves to maintain the exothermic reaction at a temperature low enough to avoid decomposition of the phosphite without the need for external cooling.

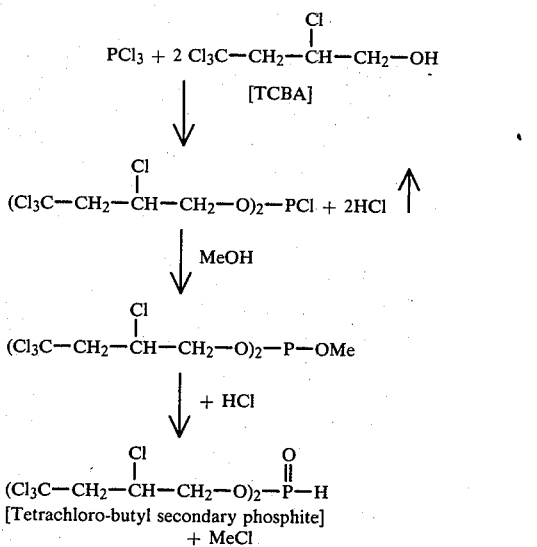

Equation II depicts another route for producing the novel tetrachloro-butyl secondary phosphites of the present invention represented by reaction of one mole of PCl$_3$ with two moles of TCBO followed by addition of one mole of a supplemental alcohol (e.g., MeOH) and subsequent cleavage and secondary phosphite formation.

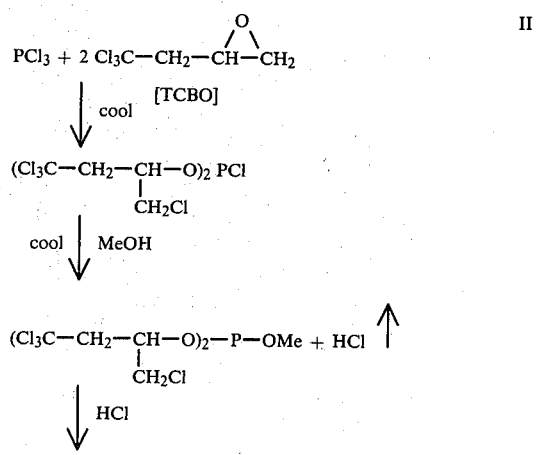

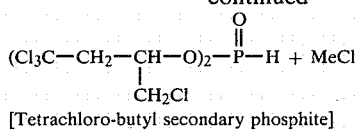

[Tetrachloro-butyl secondary phosphite]

In reaction of TCBO with a phosphorus trihalide, the alkylene oxide serves as a hydrogen halide scavenger in itself, as the hydrogen halide is utilized in the mechanism of reaction, and therefore no excess hydrogen halide is liberated. External cooling is required to maintain the exothermic reaction at a temperature low enough to avoid decomposition of the phosphite formed. In order to readily cleave the supplemental alcohol-ester group, additional hydrogen halide may be introduced to the reaction to bolster the amount generated from the supplemental alcohol reaction.

As illustrated, although both alkyl alcohols as well as alkylene oxides may be utilized in forming the phosphite esters, alcohols are preferred. The use of alcohols results in hydrogen halide generation which cools the reaction and also serves as an internal source of hydrogen halide for cleavage purposes.

In carrying out these reactions, it is contemplated that any phosphorus trihalide may be employed; i.e., the halide can be chlorine, bromine, iodine or fluorine. However, it is preferred to employ those phosphorus trihalides in which the halogen is chlorine, bromine, or mixtures thereof. Phosphorus trichloride is particularly preferred.

In addition to all TCBO or TCBA secondary phosphites derived from reaction of two moles of TCBA or TCBO per mole of phosphorus trihalide, novel secondary phosphite esters, according to the present invention, having one or more other constituents can also be readily prepared.

These compounds are represented by the formulae:

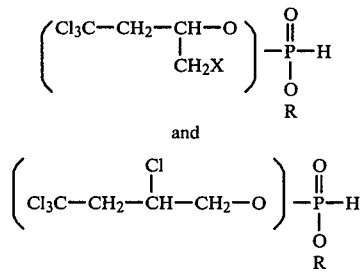

wherein X is a halogen; and, each R radical is independently selected from alkyl of 1 to about 20 carbon atoms, 2-haloalkyl of about two to about eight carbon atoms, alkaryl, aryl, halogenated aryl, and arylalkyl.

These compounds are prepared by employing reactant combinations of TCBO and TCBA, as well as combinations of other alkylene oxides, alcohols, and phenols with the TCBO and TCBA. At least one mole of TCBO or TCBA per mole of phosphorus trihalide is used, with the remaining one mole of reactant replaced with other alcohols, phenols and/or epoxides. Accordingly, aliphatic alcohols (with or without heteroatoms, such as sulfur, phosphorus, and oxygen) up to about 20 carbon atoms can be used. These typically include methanol, ethanol, butanol, isopropanol, isobutanol, 2-methoxyethanol, TCBA, other halogenated alcohols, and the like. Supplemental epoxides that can be used are alkylene oxides having a 1,2-epoxide ring. Illustrative are ethylene oxide, propylene oxide, butylene oxide, pentylene oxide, epichlorohydrin, trichloropropylene oxide, trichlorobutylene oxide, TCBO, hexylene oxide, octylene oxide, and the like. Usually, these oxides contain from two to eight, and most preferably from two to four carbon atoms. Further, phosphites containing alkaryl substituents can be prepared by including alkyl phenol reactants such as p-tert-butylphenol, nonyl phenol, 1,2,3 trimethyl phenol, 1,2 diethyl phenol, and other derivatives of phenol, naphthol, cresol, BHT, and the like. Halogenated aryl phosphite ester substituents can be accomplished through use of halogenated phenol reactants such as trihalo-phenol derivatives. Arylalkyl substituents can be made from reaction with arylalkyl alcohols such as benzyl alcohol, 2-phenyl ethanol, and other such substituted alcohols of up to about 20 carbon atoms.

In order to accommodate selective cleavage to produce a desired secondary phosphite, the supplemental alkyl alcohol or alkylene oxide employed must be of such a nature so as to form an ester group that is more susceptible to hydrogen halide cleavage than the desired secondary phosphite ester groups. Generally, the supplemental alkyl alcohol or alkylene oxide that can be used to carry out the present reactions may be any such reactant that features a lower chain length than the desired constituents. These materials typically include methanol, ethanol, isopropanol, 2-methoxyethanol, ethylene oxide, propylene oxide and the like.

Although the reaction may be run in the absence of a solvent, it is generally preferred to employ a convenient solvent medium. Any inert organic liquid which is a solvent for both the catalyst and the phosphorus trihalide may be employed for this purpose, such as ethylene dichloride.

The secondary phosphites of the present invention are useful as fire retardant additives and as chemical intermediates for fire retardant additives for epoxy, polyvinylchloride (PVC), and polyurethane resins. These phosphites further are useful as plasticizers and resin stabilizers. The high chlorine content of these phosphites results in good organic solubility, decreased water solubility, and good effectiveness in fire retardance. The products are also useful as functional fluids and lubricant additives.

The following examples are provided to further illustrate the invention. All parts and percentages given are by weight, unless otherwise specified. Temperatures given are degrees centigrade.

EXAMPLE 1

Preparation of Bis (2,4,4,4-tetrachlorobutyl) phosphite

A total of one mole distilled TCBA was added dropwise to a well-stirred solution of 0.5 mole phosphorus trichloride. The temperature of the reaction was lowered by the escaping HCl gas. The mixture was postreacted for about two hours at room temperature, and was then treated dropwise with 0.5 mole methanol. The temperature of the well-stirred mixture was kept below 35° during the addition with the aid of an ice-water bath. This final solution was post-reacted for about 30 minutes at room temperature. The HCl vapors were removed by stirring for about one hour under reduced pressure. Residual acidity was neutralized by the addition of 0.5 ml triethylamine. The colorless product thus formed was obtained in 98 percent yield. The nature of the product was substantiated by infrared, nuclear magnetic resonance, and elemental analysis. At least 61 percent of the material was the expected secondary phosphite, about 29 percent was the tertiary TCBA phosphite.

Calcd. for $C_8H_{11}Cl_8O_3P$: %Cl, 60.43; %P, 6.60. Found: %Cl, 60.67; %P, 6.47.

What is claimed is:

1. A tetrachloro-butyl secondary phosphite having the formula:

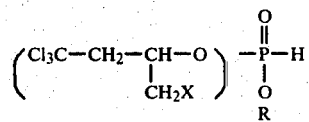

wherein X is a halogen, and R is selected from alkyl of 1 to about 20 carbon atoms, 2-haloalkyl of about 2 to about 8 carbon atoms, alkaryl, aryl, halogenated aryl, and arylalkyl.

2. The compound of claim 1 wherein R is 1,4,4,4-tetrachloro-2-butyl.

3. The compound of claim 2 wherein X is chlorine.

* * * * *